United States Patent [19]

Tanaka et al.

[11] Patent Number: 6,136,336
[45] Date of Patent: Oct. 24, 2000

[54] JM216 FORMULATIONS

[75] Inventors: Makoto Tanaka, Tama; Etsuhisa Kuwahara, Kanagawa-ken; Norimitsu Takahashi, Hachioji, all of Japan

[73] Assignee: Bristol-Myers Squibb Company, Princeton, N.J.

[21] Appl. No.: 09/444,621

[22] Filed: Nov. 22, 1999

Related U.S. Application Data

[63] Continuation of application No. 09/017,912, Feb. 3, 1998, abandoned.

[60] Provisional application No. 60/041,593, Mar. 17, 1997.

[51] Int. Cl.⁷ ........................................................ A61F 13/00
[52] U.S. Cl. .......................... 424/434; 424/422; 424/436; 424/486; 424/488; 424/499; 514/492
[58] Field of Search ..................................... 424/422, 434, 424/436, 486, 488, 499; 514/492

[56] References Cited

U.S. PATENT DOCUMENTS 5,049,686  9/1991  Hoeschele ................................ 556/137
5,661,142  8/1997  Naeger ..................................... 514/178

OTHER PUBLICATIONS

Brunner et al. Synthesis and antitumor activity of platinum (II) complexes of benzyl–1,2–diaminoethane ligands. Chem. Ber. 123 (5), 1029–38, 1990.

Lin et al. Grinding effect on some pharmaceutical properties of drugs by adding beta–cyclodextrin. drug. Dev. Ind. Pharm > 14(1), 99–118.

McKeage et al. Cancer. Chemother. Pharmac. vol.36, 451–458, 1995.

*Primary Examiner*—Thurman K Page
*Assistant Examiner*—Lakshmi Channavajjala
*Attorney, Agent, or Firm*—David M. Morse

[57] ABSTRACT

Novel suppository pharmaceutical formulations of the platinum antitumor agent, JM216, are provided. Such dosage forms provide an alternative to the oral form currently available and offer improved bioavailability of this promising drug.

3 Claims, No Drawings

JM216 FORMULATIONS

This application is a continuation of U.S. Ser. No. 09/017,912, filed Feb. 3, 1998, now abandoned, which claims the benefit of U.S. Provisional application Ser. No. 60/041,593, filed Mar. 17, 1997.

BACKGROUND OF THE INVENTION

1. Field of the Invention

The present invention relates to a novel method of increasing the aqueous solubility and bioavailability of the platinum antitumor complex, bis-acetato-ammine-dichloro-cyclohexylamine-platinum (IV), having the structural formula

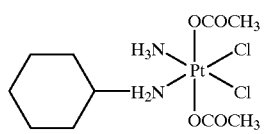

which will also be referred to below and in the claims by its literature codename, JM216. The invention also provides novel suppository dosage forms of JM216 adapted for rectal administration.

2. Description of the Prior Art

JM216 is an antitumor platinum (IV) complex presently undergoing clinical evaluation as an oral antitumor agent. The complex is described in U.S. Pat. Nos. 5,244,919 and 5,072,011.

Although the oral dosage form of JM216 being pursued in the clinic has obvious advantages over injectable platinum complexes such as cisplatin and carboplatin, it is reported by M. J. McKeage et al in Cancer Chemother. Pharmacol. 36: 451–458 (1995) that the current oral capsule form may have certain pharmacokinetic disadvantages. In a phase I clinical study $C_{max}$ and AUC increased less than proportionally to dose at dose levels $\geq 200$ mg/m². This was associated with greater interpatient pharmacokinetic variation and reduced urinary platinum recovery. Such pharmacokinetic variation and reduced gastro-intestinal drug absorption may be due to the poor water-solubility of JM216 which the present inventors have determined to be 0.3 mg/ml at 23° C.

In addition to the bioavailability problems, there are important reasons why it is often preferred to administer a drug like JM216 rectally rather than orally, e.g. nausea, vomiting and stomach irritation associated with oral dosing, inability to swallow and the possibility of partly avoiding the hapatic first pass clearance.

SUMMARY OF THE INVENTION

This invention relates to a method of improving the aqueous solubility and thus absorption and bioavailability of JM216 pharmaceutical formulations, which comprises employing in said formulations amorphous JM216. The amorphous JM216 is obtained by grinding or milling JM216 powder with β-cyclodextrin or certain polymers for a sufficient period of time to convert the JM216 to an amorphous state, the polymer being preferably selected from gelatin, polyvinylpyrrolidinone (PVP) and hydroxypropylmethyl cellulose (HPMC).

In another aspect the invention relates to a suppository formulation for rectal administration comprising:

(a) JM216

(b) a polyethylene glycol (PEG) suppository base, and (c) a fatty acid selected from caproic acid or its sodium salt, caprylic acid or its sodium salt and the sodium salt of oleic acid.

The suppository formulation of the present invention may optionally contain a surface active agent and the JM216 may be employed in an amorphous state obtained by grinding or milling JM216 powder with β-cyclodextrin or a polymer selected from gelatin, polyvinylpyrrolidinone and hydroxypropylmethyl cellulose.

DETAILED DESCRIPTION OF THE INVENTION

JM216 is a platinum antitumor complex having poor water-solubility. This low solubility may be associated with bioavailability problems seen in a recent phase I clinical study where the compound was orally administered in the form of hard gelatin capsules with excipients (microcrystalline cellulose, sodium starch glycolate, lactose anhydrous and magnesium stearate).

It was an object of the present invention to find a way of increasing the aqueous solubility of JM216 so as to improve the bioavailability of the compound and perhaps also eliminate or reduce side effects seen with oral dosing such as nausea and vomitting. It was another object of the invention to develop a suppository dosage formulation of JM216 which could provide the same therapeutic advantages of the existing oral formulation while also improving the bioavailability. It was hoped that the suppository formulation would also have an improved side-effect profile as well as being an alternate dosage form for those patients who cannot tolerate oral dosing, e.g. infant patients or patients with disorders of the digestive organs.

The present inventors first attempted to reduce the particle size of the JM216 powder obtained from chemical synthesis by grinding or milling it to an amorphous state (as confirmed by x-ray diffraction pattern). The amorphous state indicates the disappearance of particles or crystalline drug and a particle size close to the molecular level. However, it was found to be very difficult to obtain an amorphous state by simply grinding the drug alone owing to the re-aggregation of drug powder by electrostatic force during the grinding process. The addition of β-cyclodextrin or polymers to the JM216 during the grinding did allow obtaining the drug as an amorphous powder by reduction of the aggregation. Interestingly, the effect on solubility was quite dependent on the polymer used, with gelatin, polyvinylpyrrolidinone and hydroxypropylmethyl cellulose showing marked improvement of dissolution rate over drug alone. The ratio of drug:β-cyclodextrin or drug:polymer also has some effect on solubility, with solubility generally increasing at higher β-cyclodextrin:drug or polymer:drug ratios. Ratios of drug:β-cyclodextrin or drug:polymer of from about 1:1 to about 1:15 (w/w) can be used with ratios of from about 1:4 to 1:15 being preferred and ratios of from about 1:9 to about 1:15 being most preferred. Table I below shows dissolution results when various JM216:polymer or JM216:β-cyclodextrin mixtures, after grinding with an automatic mortar for three hours, were evaluated in a standard dissolution test.

TABLE 1

| Dissolution of JM216 | | | | | |
|---|---|---|---|---|---|
| | Dissolved JM216 (mg/ml) | | | | |
| | 1 Min. | 5 Min. | 15 Min. | 30 Min. | 60 Min. |
| JM216 bulk drug alone | 0.2 | 0.3 | 0.5 | 0.5 | 0.5 |
| JM216:gelatin (1:9, w/w) | 1.4 | 1.2 | 1.2 | 1.1 | 1.1 |
| JM216:gelatin (1:4, w/w) | 1.1 | 1.1 | 1.0 | 0.9 | 1.0 |
| JM216:gelatin (1:1, w/w) | 0.5 | 0.6 | 0.7 | 0.7 | 0.6 |
| JM216:HPMC (1:9, w/w) | 0.9 | 1.1 | 1.0 | 0.9 | 0.9 |

TABLE 1-continued

Dissolution of JM216

| | Dissolved JM216 (mg/ml) | | | | |
|---|---|---|---|---|---|
| | 1 Min. | 5 Min. | 15 Min. | 30 Min. | 60 Min. |
| JM216:HPMC (1:4, w/w) | 0.7 | 0.8 | 0.7 | 0.7 | 0.7 |
| JM216:HPMC (1:1, w/w) | 0.6 | 0.7 | 0.6 | 0.6 | 0.6 |
| JM216:PVP (1:9, w/w) | 0.8 | 0.9 | 1.0 | 0.9 | 0.9 |
| JM216:Pullulan (1:9, w/w) | 0.5 | 0.8 | 0.7 | 0.7 | 0.7 |
| JM216:PEG 6000 (1:9, w/w) | 0.5 | 0.5 | 0.5 | 0.5 | 0.5 |
| JM216:Avicel (1:9, w/w) | 0.7 | 0.7 | 0.7 | 0.7 | 0.7 |
| JM216:Lactose (1:9, w/w) | 0.7 | 0.7 | 0.7 | 0.7 | 0.7 |
| JM216:β-cyclodextrin (1:9, w/w) | 0.9 | 0.9 | 0.9 | 0.9 | 0.9 |

HPMC = hydroxypropylmethyl cellulose,
PVP = polyvinylpyrrolidone,
PEG = polyethylene glycol,
Pullulan = natural polysaccharide,
Avicel is the tradename of FMC Corporation for microcrystalline cellulose.

Dissolution test: The ground mixture containing 5 mg. of JM216 was transferred directly into 50 ml of phosphate buffer (1/15 M, pH 7.5) kept at 37° C. and was stirred with a magnetic stirrer bar at 300 rpm. An aliquot of the solution was pipetted at the indicated time intervals and filtered through a 0.45 μm membrane filter. The concentration of the dissolved JM216 was determined by high performance liquid chromatography (HPLC).

Grinding of the JM216:β-cyclodextrin or JM216:polymer mixtures may be accomplished by standard procedures, e.g. automatic mortar and pestle machines or a hybridizer (milling machine). The time needed in the grinding process may be readily determined by simple test (period analysis of the mixture by x-ray diffraction studies). A suitable grinding time with the automatic mortar and pestle machine is three hours and with the hybridizer, five minutes.

As can be seen from Table I, use of amorphous JM216 with β-cyclodextrin or certain polymer additives significantly increases the water-solubility of JM216. The preferred formulations with increased solubility are those where the JM216 is ground to an amorphous state in the following drug:β-cyclodextrin or drug:polymer ratios:

JM216:gelatin in ratios of from about 1:4 to about 1:9 (w/w);
JM216:HPMC in a 1:9 (w/w) ratio;
JM216:PVP in a 1:9 (w/w) ratio; and
JM216:β-cyclodextrin in a 1:9 (w/w) ratio.

Such formulations result in approximately a doubling of the aqueous solubility over bulk JM216 powder alone and are one important aspect of the present invention. Such amorphous JM216 can be used in a wide variety of JM216 pharmaceutical formulations, including both oral and non-oral forms, to improve the bioavailability of JM216.

The present inventors also explored developing a suppository dosage form of JM216 which would provide an alternative dosage form for those patients unable to use the current oral capsules. It was a goal to develop such a suppository dosage form which would have better absorption than the oral form and reduced side effects, e.g. nausea and vomitting.

In their studies in vitro drug absorption of the test formulations was examined using excised rat rectum in accordance with the method described by T. Ogiso et al in *J. Pharmacobio-Dyn.*, 14, 385 (1991). The rectum was freshly excised from each rat and was opened lengthwise using scissors. The excised rectum, serous membrane side down, was mounted on a Franz diffusion cell (reservoir volume 10 ml, 7 mm i.d. O ring flange). Each preparation (80 mg., 2 mg as JM216) was uniformly applied to the mucosal side and was occluded with a sheet of aluminum foil. Gentamicin solution (10 mg/ml) was added to the reservoir fluid (phosphate buffer, pH 7.3) in the ratio of 1:100. The assembly was incubated at 37° C. and aliquots (200 μl) of the reservoir fluid were periodically withdrawn for 23 hours. The amount of JM216 permeated through rat rectum was determined by HPLC.

The various test samples were incorporated into standard suppository bases and then subjected to the in vitro drug absorption test. In addition, JM 216 powder alone and the ground anhydrous JM216:β-cyclodextrin or JM216:polymer mixture suspended in water were also subjected to the tests. The suppository samples were prepared by fusion method melting the base at 50° C. for fatty bases or at 75° C. for polyethylene glycol water-soluble base. The drug was incorporated into the base at a concentration of 2 mg/80 mg base. Medium chain fatty acids (or Na salts thereof) and surface active agents were also added at the appropriate level.

The results in the rat rectum absorption model are as shown below in Table II.

TABLE II

JM216 ABSORPTION THROUGH EXCISED RAT RECTUM

| Drug | Additives | Suppository Bases | JM216 Absorbed (%) | | | |
|---|---|---|---|---|---|---|
| | | | 14 h | 17 h | 20 h | 23 h |
| JM216 (non-amorphous) | | Water | 0.0 | 0.0 | 0.0 | 0.0 |
| JM216 (non-amorphous) | | Witepsol H-15 | 0.0 | 0.0 | 0.0 | 0.0 |
| JM216 (non-amorphous) | | Pharmasol | 0.0 | 0.0 | 0.0 | 0.0 |
| JM216 (non-amorphous) | | Isocacao | 0.0 | 0.0 | 0.0 | 0.2 |
| JM216 (non-amorphous) | | Miglyol | 0.0 | 0.0 | 0.0 | 0.0 |
| JM216 (non-amorphous) | | PEG | 0.2 | 0.5 | 0.9 | 1.2 |
| JM216 (non-amorphous) | | PEG + Pharmasol | 0.0 | 0.0 | 0.0 | 0.3 |
| JM216 (non-amorphous) | 3%, capryl-Na | PEG | 7.5 | 8.6 | 10.5 | 11.5 |
| JM216 | 3%, BL-21 | PEG | 1.8 | 4.6 | 5.2 | 6.2 |

TABLE II-continued

JM216 ABSORPTION THROUGH EXCISED RAT RECTUM

| Drug | Additives | Suppository Bases | JM216 Absorbed (%) | | | |
|---|---|---|---|---|---|---|
| | | | 14 h | 17 h | 20 h | 23 h |
| (non-amorphous) | | | | | | |
| JM216 (non-amorphous) | 3%, BLYK | PEG | 0.6 | 1.1 | 1.3 | 3.7 |
| JM216 (non-amorphous) | 3%, BL-21 | Pharmasol | 0.1 | 0.3 | 0.6 | 0.8 |
| JM216 (non-amorphous) | 3%, GLYK | Pharmasol | 0.0 | 0.0 | 0.1 | 0.3 |
| JM216:gelatin (1:9) | | Water | 0.0 | 0.0 | 0.1 | 0.3 |
| JM216:gelatin (1:9) | | PEG | 0.2 | 0.6 | 1.8 | 3.8 |
| JM216:gelatin (1:9) | | Pharmasol | 0.0 | 0.0 | 0.1 | 0.3 |
| JM216:gelatin (1:9) | | Miglyol | 0.0 | 0.0 | 0.2 | 0.7 |
| JM216:gelatin (1:9) | 3%, caproic acid | PEG | 1.8 | 2.8 | 3.6 | 5.0 |
| JM216:gelatin (1:9) | 3%, caprylic acid | PEG | 5.2 | 6.5 | 7.9 | 9.4 |
| JM216:gelatin (1:9) | 3%, capric acid | PEG | 1.2 | 1.8 | 2.9 | 4.1 |
| JM216:gelatin (1:9) | 3%, oleic acid | PEG | 0.7 | 1.4 | 2.2 | 3.2 |
| JM216:gelatin (1:9) | 3%, linoleic acid | PEG | 0.8 | 1.4 | 2.2 | 3.3 |
| JM216:gelatin (1:9) | 3%, linolenic acid | PEG | 0.2 | 0.6 | 1.2 | 1.8 |
| JM216:gelatin (1:9) | 3%, caproic-Na | PEG | 5.9 | 9.5 | 11.3 | 14.6 |
| JM216:gelatin (1:9) | 3%, capric-Na | PEG | 2.4 | 3.6 | 4.3 | 6.4 |
| JM216:gelatin (1:9) | 3%, lauric-Na | PEG | 1.5 | 2.2 | 3.4 | 4.9 |
| JM216:gelatin (1:9) | 3%, oleic-Na | PEG | 2.0 | 3.1 | 3.5 | 5.3 |
| JM216:gelatin (1:9) | 3%, capryl-Na | miglyol | 0.1 | 0.2 | 0.4 | 0.8 |
| JM216:gelatin (1:9) | 3%, capryl-Na | PEG + miglyol* | 2.5 | 3.7 | 4.8 | 6.1 |
| JM216:gelatin (1:9) | 1%, capryl-Na | PEG | 3.8 | 5.3 | 6.5 | 7.5 |
| JM216:gelatin (1:9) | 3%, capryl-Na | PEG | 7.0 | 9.0 | 10.8 | 13.2 |
| JM216:gelatin (1:9) | 7%, capryl-Na | PEG | 2.3 | 3.0 | 4.0 | 4.8 |
| JM216:gelatin (1:9) | 3%, GLYK | PEG | 0.1 | 0.7 | 1.3 | 1.9 |
| JM216:gelatin (1:9) | 3%, pluronic | PEG | 0.3 | 0.5 | 0.8 | 1.2 |
| JM216:gelatin (1:9) | 3%, capryl-Na +3%, pluronic | PEG | 6.6 | 8.6 | 10.1 | 11.1 |
| JM216:gelatin (1:9) | 3%, capryl-Na +3%, Tween 80 | PEG | 5.7 | 7.4 | 8.8 | 9.5 |
| JM216:gelatin (1:9) | 3%, capryl-Na +3%m BL-21 | PEG | 1.5 | 2.5 | 3.2 | 4.3 |
| JM216:β-cyclodextrin (1:9) | 3%, capryl-Na | PEG | 0.3 | 0.8 | 1.6 | 2.0 |
| JM216:β cyclodextrin (1:9) | 3%, pluronic | PEG | 1.1 | 2.0 | 2.7 | 3.2 |
| JM216:HPMC (1:9) | 3%, capryl-Na | PEG | 1.5 | 2.1 | 3.7 | 4.3 |

*Miglyol was used here as an additive to change the nature of the PEG suppository base. The base gradually dissolves in water because of the addition of Miglyol. It is prepared by adding 3–10% of Miglyol to PEG at 75° C. mixing (stirring) with 1–5% pluronic F68. The actual formulation of base used here was PEG + 3% pluronic F68 + 5% Miglyol. Tween 80 could be substituted for the pluronic F68.
Witepsol H15 = fatty suppository base manufactured by Hüls Aktiengesellsch
Pharmasol = fatty suppository base manufactured by Nippon Oil & FAts Co., Ltd.
Isocacao = fatty suppository base manufactured by Kao Co.
Miglyol = Medium chain fatty acid triglyceride suppository base manufactured by Hüls Aktiengesellsch
PEG = Polyethylene glycol (water-soluble suppository base)
Capryl-Na = Sodium caprylate (fatty acid)
BL-21 = Polyoxyethylene (21) lauryl ether (surface active agent)
GLYK = Dipotassium glycyrrhizinate (surface active agent)
Caproic acid (fatty acid)
Caprylic acid (fatty acid)
Capric acid (fatty acid)
Oleic acid (fatty acid)
Linoleic acid (fatty acid)
Linolenic acid (fatty acid)
Capric-Na = sodium caprate (fatty acid)
Lauric-Na = sodium laurate (fatty acid)
Oleic-Na = sodium oleate (fatty acid)
Caproic-Na = sodium caproate (fatty acid)
Pluronic = F68 (poloxamer) (surface active agent)
Tween 80 = polysorbate 80 = a surface active agent Looking at the results of this study, JM216 bulk drug (non-amorphous) was little absorbed in the form of a suspension in water or in fatty suppository bases. The drug alone was, however, absorbed to some extent when incorporated into the water-soluble base, polyethylene glycol (PEG). PEG was thus determined to be the most appropriate suppository base for JM216. PEG having molecular weights of from about 400–6000 is preferred (the PEG used in the above study was a mixture of 400, 1500 and 4000 (2:1:5, w/w) molecular weight material).

Based on their experience, the present inventors determined that in the rat rectum absorption model a percentage absorption of 4% or greater was considered necessary for a commercially useful suppository formulation of JM216.

Addition of certain fatty acids to the PEG suppository base containing non-amorphous JM216 gave the desired absorption levels while similar PEG formulations without these fatty acids were unacceptable. The amorphous JM216 produced by grinding or milling JM216 with β-cyclodextrin or polymers, particularly gelatin, HPMC or PVP, can also be added to a PEG suppository base and certain fatty acids, particulary caproic acid or its sodium salt, caprylic acid or its sodium salt, capric acid or its sodium salt and the sodium salt of oleic acid, to obtain a suppository dosage form having excellent absorption properties. The fatty acid is used in an amount of from 0.5 to 10% (w/w) of the total suppository weight.

Addition of surface active agents to the suppositories employing a PEG base, amorphous JM216 and a fatty acid selected from caproic acid or its sodium salt, caprylic acid or its sodium salt, capric acid or its sodium salt and the sodium salt of oleic acid also resulted in suppository formulations showing high absorption. Again, in the case of amorphous JM216, material made by grinding JM216 with gelatin, HPMC, PVP or β-cyclodextrin, is preferred for achieving the best absorption results. The surface active agent is employed in an amount of from 0.5 to 7% of the total suppository weight. Preferred surface active agents include Tween 80 and pluronic (e.g. pluronic F68).

The JM216, whether amorphous or non-amorphous, is used in an amount of from 0.1 to 10% (w/w) of the total suppository weight.

Particularly preferred suppository formulations according to the present invention include the following:

JM216:gelatin (1:9, w/w), PEG suppository base, 3% capryl Na

JM216:gelatin (1:9, w/w), PEG suppository base, 3% capryl Na, 3% pluronic surface active agent JM216:gelatin (1:9, w/w), PEG suppository base, 3% capryl Na, 3% Tween 80 surface active agent JM216:gelatin (1:9, w/w), PEG suppository base, 3% caproic Na JM216:gelatin (1:9, w/w), PEG suppository base, 3% caprylic acid JM216 (non-amorphous), PEG suppository base, 3% capryl Na The suppository formulations are prepared by mixing of the JM216 and fatty acid with a PEG suppository base by any recognized method of making suppositories using water-soluble PEG bases. The surface active agents and other excipients such as Miglyol can also be added to the mixture. The dosage amount of JM216 in the suppository formulation is sufficient to insure the release of sufficient dosage units of JM216 into the blood to provide the desired therapeutic effect and may be readily determined by those skilled in the art by simple test.

EXAMPLES

Example 1

Preparation of JM216 suppository using sodium salt of fatty acid

Formulation: JM216:gelatin (1:9, w/w)+3% caproic-Na+PEG

PEG400, PEG1500 and PEG6000 were mixed in a ratio of 2:1:5 (w/w) and then melted at 75° C. The ground mixture (20 g) of JM216 and gelatin (1:9, w/w) was added to the melted PEG mixture (57.6 g) and stirred until the ground mixture was dispersed homogeneously. Sodium caproate (2.4 g) was added and then stirred for a short time at 70° C. The mass was immediately poured into molds and allowed to solidify at room temperature. The above process was carried out in a light-free environment.

Example 2

Preparation of JM216 suppository using free fatty acid

Formulation: JM216:gelatin (1:9, w/w)+3% caprylic acid+PEG

PEG400, PEG1500 and PEG6000 were mixed in a ratio of 2:1:5 (w/w) and then melted at 75° C. The ground mixture (20 g) of JM216 and gelatin (1:9, w/w) was added to the melted PEG mixture (57.6 g) and stirred until the ground mixture was dispersed homogeneously. Caprylic acid (2.4 g) was added and then stirred for a short time at 70° C. The mass was immediately poured into molds and allowed to solidify at room temperature. The entire process was carried out in a light-free environment.

Example 3

Preparation of JM216 suppository using surface active agent

Formulation: JM216:gelatin (1:9, w/w)+3% capryl-Na+3% pluronic F68+PEG

PEG400, PEG1500 and PEG6000 were mixed in a ratio of 2:1:5 (w/w) and then melted at 75° C. Pluronic F68 (2.4 g) was added to the melted PEG mixture (55.2 g) and stirred vigorously. The ground mixture (20 g) of JM216 and gelatin (1:9, w/w) was added to the mixture and stirred until the ground mixture was dispersed homogeneously. Sodium caprylate (2.4 g) was added and then stirred for a short time at 70° C. The mass was immediately poured into molds and allowed to solidify at room temperature. The entire process was carried out in a light-free environment.

We claim:

1. A suppository formulation for rectal administration comprising
   (a) bis-acetato-ammine-dichloro-cyclohexylamine-platinum (IV),
   (b) a polyethylene glycol suppository base, and
   (c) a fatty acid,
wherein the fatty acid is selected from the group consisting of
   (1) sodium caprylate in an amount of
   (2) caproic acid in an amount of 3%
   (3) caprylic acid in an amount of 3%
   (4) capric acid in an amount of 3%
   (5) sodium caproate in an amount of 3%
   (6) sodium caprate in an amount of 3%
   (7) sodium laurate in an amount of 3%
   (8) sodium oleate in an amount of 3%
   (9) sodium caprylate in an amount of 1%; and
   (10) sodium caprylate in an amount of 7%.

2. A suppository formulation according to claim 1 wherein there is also employed a surface active agent.

3. A suppository formulation according to claim 1 or claim 2 wherein the bis-acetato-ammine-dichloro-cyclohexylamine-platinum (IV) employed is in an amorphous state obtained by grinding with gelatin, polyvinylpyrrolidinone, hydroxypropylmethyl cellulose or β-cyclodextrin.

* * * * *